United States Patent [19]

Blanchard et al.

[11] 4,133,816

[45] Jan. 9, 1979

[54] PREPARATION OF CIS-1-HYDROXY-3-SUBSTITUTED-6,6-DIMETHYL-6,6A,7,8,10,10A-HEXAHYDRO-9H-DIBENZO[b,d]PYRAN-9-ONES AND INTERMEDIATES THEREFOR

[75] Inventors: William B. Blanchard; Charles W. Ryan, both of Indianapolis, Ind.

[73] Assignee: Eli Lilly and Company, Indianapolis, Ind.

[21] Appl. No.: 904,702

[22] Filed: May 10, 1978

Related U.S. Application Data

[62] Division of Ser. No. 814,817, Jul. 12, 1977, which is a division of Ser. No. 702,804, Jul. 6, 1976, Pat. No. 4,054,581.

[51] Int. Cl.$^2$ ............................................. C07D 319/04
[52] U.S. Cl. .................................................. 260/340.7
[58] Field of Search ....................................... 260/340.7

[56] References Cited

U.S. PATENT DOCUMENTS

| 3,127,417 | 3/1964 | Porret et al. .................... 260/340.7 |
| 4,054,581 | 10/1977 | Blanchard et al. ........... 260/340.7 X |

OTHER PUBLICATIONS

Chem. Abstracts 77:75177m.

*Primary Examiner*—Ethel G. Love
*Attorney, Agent, or Firm*—Charles W. Ashbrook; Everet F. Smith

[57] ABSTRACT

Reaction of a 5-substituted resorcinol with a ketal of 4-(1-hydroxy)-1-methylethyl)-3-cyclohexen-1-one in the presence of a suitable catalyst effects condensation to provide substantially exclusively a cis-1-hydroxy-3-substituted-6,6-dimethyl-6,6a,7,8,10,10a-hexahydro-9H-dibenzo[b,d]pyran-9-one.

4 Claims, No Drawings

PREPARATION OF CIS-1-HYDROXY-3-SUBSTITUTED-6,6-DIMETHYL-6,6A,7,8,10,10A-HEXAHYDRO-9H-DIBENZO[b,d]PYRAN-9-ONES AND INTERMEDIATES THEREFOR

This is a division of application Ser. No. 814,817, filed July 12, 1977, which was a division of application Ser. No. 702,804, filed July 6, 1976, now U.S. Pat. No. 4,054,581.

BACKGROUND OF THE INVENTION

Certain dibenzopyranones are useful pharmacological agents. It recently has been found that trans-1-hydroxy-3-alkyl-6,6-dimethyl-6,6a,7,8,10,10a-hexahydro-9H-dibenzo[b,d]pyran-9-ones are especially useful in the treatment of pain, anxiety, and depression, see U.S. Pat. Nos. 3,928,598, 3,944,673, and 3,953,603. Such compounds can be prepared, according to the disclosure by Fahrenholtz, Lurie and Kierstead, *J. Am. Chem. Soc.* 88, 2079(1966), 89, 5934(1967), by reacting a 5-alkyl resorcinol with diethyl α-acetylglutarate to form an ethyl 4-methyl-5-hydroxy-7-alkyl coumarin-3-propionate. The coumarin derivative can be reacted with a metal hydride to effect cyclization to the corresponding 1-hydroxy-3-alkyl-7,10-dihydro-6H-dibenzo-[b,d]pyran-6,9(8H)dione. Ketalization of the 9-keto group followed by reaction with methyl magnesium bromide and deketalization affords the corresponding 1-hydroxy-3-alkyl-6,6-dimethyl-6,6a,7,8-tetrahydro-9H-dibenzo[b,d]pyran-9-one. Reduction of the latter compound provides predominantly the corresponding trans-1-hydroxy-3-alkyl-6,6-dimethyl-6,6a,7,8,10,10a-hexahydro-9H-dibenzo[b,d]pyran-9-one, with minor quantities of the less active 6a,10a-cis-isomer being formed. Such process for preparing trans-dibenzopyranones suffers from being multistep and of low overall yield, in addition to requiring separation of the trans isomer from the cis isomer.

It recently has been discovered that cis-hexahydrodibenzopyranones can be converted to the corresponding trans isomer, and the cis-hexahydrodibenzopyranones can be prepared in high yield in only one step. More particularly, a cis-1-hydroxy-3-substituted-6,6-dimethyl-6,6a,7,8,10,10a-hexahydro-9H-dibenzo[b,d]pyran-9-one can be reacted with an aluminum halide in an organic solvent to effect epimerization to provide the corresponding trans-hexahydrodibenzopyranone. Such process is the subject of our copending application filed this even date herewith. The reaction of a 5-substituted resorcinol with 1-methoxy-4-(1-hydroxy-1-methylethyl)-1,4-cyclohexadiene in the presence of a catalyst such as boron trifluoride diethyl etherate or stannic chloride to provide a cis-1-hydroxy-3-substituted-6,6-dimethyl-6,6a,7,8,10,10a-hexahydro-9H-dibenzo[b,d]-pyran-9-one is the subject of Day and Lavagnino's copending application filed this even date herewith.

An object of this invention is to provide an alternate process for preparing substantially exclusively cis-hexahydrodibenzo[b,d]pyran-9-ones, utilizing novel compounds which are ketals of 4-(1-hydroxy-1-methylethyl)-3-cyclohexen-1-one.

SUMMARY OF THE INVENTION

This invention provides a process for preparing a hexahydrodibenzopyranone of the formula

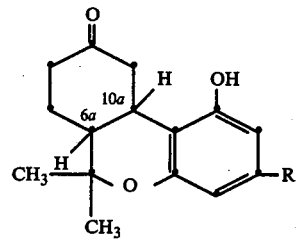

wherein R is $C_5$–$C_{10}$ alkyl, $C_5$–$C_{10}$ alkenyl, $C_5$–$C_8$ cycloalkyl, or $C_5$–$C_8$ cycloalkenyl, and wherein the hydrogen atoms attached at the 6a and 10a positions are oriented cis to one another, comprising reacting a 5-substituted resorcinol of the formula

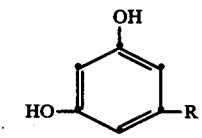

wherein R has the above-defined meaning, and a 4-(1-hydroxy-1-methylethyl)-3-cyclohexenone ketal of the formula

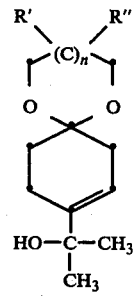

wherein n is 0 or 1, R' and R" independently are hydrogen, methyl or ethyl; in the presence of a catalyst selected from the group consisting of boron tribromide, boron trifluoride, and stannic chloride, in an organic solvent at a temperature within the range of from about −20° C. to about 100° C., for a period of time of from about 0.5 to about 8 hours, and recovering the product therefrom. Cyclohexenone ketals having the above formula are new compounds provided by this invention.

DETAILED DESCRIPTION OF THE INVENTION

According to the process of this invention, a ketal of 4-(1-hydroxy-1-methylethyl)-3-cyclohexen-1-one is reacted with a 5-substituted resorcinol in the presence of a suitable catalyst and in an organic solvent. The quantities of the cyclohexenone derivative and the resorcinol derivative incorporated in the present process generally are approximately equimolar quantities; however, an excessive quantity of either reactant can be utilized if desired. The process is carried out in the presence of a suitable catalyst such as boron trifluoride, boron tribromide, and stannic chloride. Especially preferred catalysts include boron trifluoride, generally as the commercially available diethyletherate complex, and stannic chloride. The quantity of catalyst generally utilized in the present process ranges from about an equimolar quantity to about a 1 to 6 molar excess; however, the precise amount of catalyst used is not critical. A preferred quantity of catalyst utilized in the process is about a 2 to about a 4 molar excess. The process typically is carried out in organic solvents such as halogenated hydrocarbons, aromatic solvents, ethers, and the like. Especially preferred solvents include dichloromethane, 1,1-dichloroethane, 1,2-dibromoethane, 1,2-dichloroethane, 1-chloropropane, 2-bromopropane, chlorobenzene, benzene, xylene, toluene, diethyl ether, and methyl ethyl ether. Normally the process of this invention is carried out at a temperature ranging from about −20° C. to about 100° C., and is most conveniently conducted at about −10° C. to about 40° C. The reaction between the cyclohexenone ketal and the 5-substituted resorcinol in accordance with the process of this invention generally is substantially complete within about 0.5 to about 8.0 hours; however, longer reaction times are not detrimental to the product of the reaction and can be employed if desired. Upon completion of the reaction, the product, a dl-cis-1-hydroxy-3-substituted-6,6-dimethyl-6,6a,7,8,10,10a-hexahydro-9H-dibenzo[b,d]pyran-9-one, is readily isolated by simply washing the reaction mixture with water, or if desired by washing the reaction mixture successively with a dilute aqueous base and a dilute aqueous acid, and then removing the reaction solvent from the washed reaction mixture, for instance by evaporation under reduced pressure. The product dl-cis-hexahydrodibenzopyranone generally needs no further purification, eventhough small quantities of the dl-trans isomer, on the order of about 1 to about 5 percent by weight, are generally detectable. Separation of such cis and trans isomers is unnecessary since the product of the process of this invention is treated with an aluminum halide such as aluminum chloride in a solvent such as dichloromethane in order to effect complete epimerization of the dl-cis-hexahydrodibenzopyranone to the corresponding dl-trans-hexahydrodibenzopyranone. For example, the dl-cis-1-hydroxy-3-(1,1-dimethylheptyl)-6,6-dimethyl-6,6a,7,8,10,10a-hexahydro-9H-dibenzo[b,d]pyran-9-one prepared in accordance with the process of this invention can be dissolved in dichloromethane and treated with about a 3 to 4 molar excess of aluminum chloride at a temperature of about 25° C. for a period of time of from about 1 to about 4 hours. The product of such conversion, dl-trans-1-hydroxy-3-(1,1-dimethylheptyl)-6,6-dimethyl-6,6a,7,8,10,10a-hexahydro-9H-dibenzo[b,d]pyran-9-one, is particularly useful in the treatment of anxiety and depression as hereinbefore described.

The starting materials required to carry out the process of this invention are either available or readily preparable by known procedure. For example, the 5-substituted resorcinols which are utilized in the process of this invention are available by the methods taught by Adams et al., see for example *J. Am. Chem. Soc.*, 70, 644(1948). The ketals of 4-(1-hydroxy-1-methylethyl)-3-cyclohexen-1-one which are reacted with a 5-substituted resorcinol according to the process of this invention are new compounds and are a further aspect of this invention. Such compounds are prepared, in general, by reacting a methyl Grignard reagent such as methyl magnesium bromide with the appropriate ketal of 4-methoxycarbonyl-3-cyclohexen-1-one. Ketals of 4-methoxycarbonyl-3-cyclohexen-1-one are prepared according to the process of Danishefsky et al., *J. Am. Chem. Soc.*, 96, 7807(1974), and *J. Org. Chem*, 40, 538(1975). Specifically, 1-methoxy-3-trimethylsilyloxy-1,3-butadiene is reacted with methyl acrylate to provide 3-methoxy-4-methoxycarbonyl-1-trimethylsilyloxy-1-cyclohexene. Reaction of the latter compound with a glycol such as 1,2-ethanediol, 1,3-propanediol, 2,2-dimethyl-1,3-propanediol, 2-methyl-2-ethyl-1,3-propanediol, or 2,2-diethyl-1,3-propanediol, in the presence of an acid such as paratoluenesulfonic acid, effects loss of methanol, hydrolysis of the trimethylsilyl group, and concomitant ketalization to provide the corresponding ketal of 4-methoxycarbonyl-3-cyclohexen-1-one. Reaction of such ketal with a methyl Grignard reagent under normal reaction conditions then provides the corresponding tertiary alcohol, namely a ketal of 4-(1-hydroxy-1-methylethyl)-3-cyclohexen-1-one. For example, reaction of the 2,2-dimethyl-1,3-propanediol ketal of 4-methoxycarbonyl-3-cyclohexen-1-one with methyl magnesium bromide in a solvent such as diethyl ether for about two hours, followed by treatment of the reaction mixture with aqueous ammonium chloride solution and removal of the reaction solvent, provides the corresponding tertiary alcohol, namely the 2,2-dimethyl-1,3-propanediol ketal of 4-(1-hydroxy-1-methylethyl)-3-cyclohexen-1-one. Such compounds generally need no further purification, but if desired can be distilled or chromatographed under normal conditions.

In order to demonstrate more fully the operation of the invention, the following detailed examples are provided by way of illustration.

EXAMPLE 1

α,α-Dimethyl-1,4-dioxaspiro[4.5]dec-7-ene-8-methanol; the ethylene ketal of 4-(1-hydroxy-1-methylethyl)-3-cyclohexen-1-one A solution of 11.0 g. of the ethylene ketal of 4-methoxycarbonyl-3-cyclohexen-1-one in 100 ml. of toluene was added dropwise over thirty minutes to a stirred solution of 110 millimoles of methyl magnesium bromide in diethyl ether. The reaction mixture was stirred for two hours at about 15° C., and then was cooled to 5° C. and added to 100 ml. of a 1.3 molar aqueous solution of ammonium chloride. The organic phase was separated, washed with water, dried, and the solvent was removed therefrom by evaporation under reduced pressure to provide 6.6 g. of the ethylene ketal of 4-(1-hydroxy-1-methylethyl)-3-cyclohexen-1-one.

Analysis Calc. for $C_{11}H_{18}O_3$. Theory: C, 66.64; H, 9.15; O, 24.21. Found: C, 66.68; H, 9.05; O, 24.30.

nmr (CDCl$_3$): δ1.3 (s, 6H, C(CH$_3$)$_2$). δ2.6 (s, 1H, OH).

Following the procedure set forth in Example 1, there was prepared α,α-3,3-tetramethyl-1,5-dioxaspiro[5.5]-undec-8-ene-9-methanol, the 2,2-dimethyl-1,3-propanediol ketal of 4-(1hydroxy-1-methylethyl)-3-cyclohexen-1-one. M.P. 114° C.

Analysis Calc. for $C_{14}H_{24}O_3$. Theory: C, 69.96; H, 10.07; O, 19.97. Found: C, 70.17; H, 10.11; O, 20.07.

nmr (CDCl$_3$): δ1.3 (s, 6H, C(CH$_3$)$_2$—OH). δ1.0 (2s, 3H each, C—C(CH$_3$)$_2$—C).

EXAMPLE 2 dl-cis-1-hydroxy-3-(1,1-dimethylheptyl)-6,6-dimethyl-6,6a,7,8,10,10a-hexahydro-9H-dibenzo[b,d]pyran-9-one A solution of 2.30 g. of the ethylene ketal of 4-(1hydroxy-1-methylethyl)-3-cyclohexen-1-one and 2.12 g. of 5-(1,1-dimethylheptyl)resorcinol in 50 ml. of commercial grade dichloromethane was stirred and cooled to −10° C. in an ice/acetone bath. To the cold stirred reaction mixture was added 3.6 ml. of stannic chloride dropwise over a five minute period. During the addition of the stannic chloride, the temperature of the reaction mixture increased from −10° C. to 0° C. Following complete addition of the stannic chloride to the reaction mixture, the mixture was stirred for four hours while maintaining the temperature at 0 to 5° C. The reaction mixture next was warmed to about 25° C. and stirred an additional two hours. The reaction mixture was then washed with water and with 1N sodium hydroxide solution, and dried. Removal of the solvent by evaporation under reduced pressure afforded a solid residue, which was then crystallized from 20 ml. of n-hexane to provide 2.66 g. of dl-cis-1-hydroxy-3-(1,1-dimethylheptyl)-6,6-dimethyl-6,6a,7,8,10,10a-hexahydro-9H-dibenzo[b,d]pyran-9-one. M.P. 160–162° C. GLC demonstrated the product to contain 89.0 percent of the title compound.

EXAMPLE 3 dl-cis-1-hydroxy-3-(1,1-dimethylheptyl)-6,6-dimethyl-6,6a,7,8,10,10a-hexahydro-9H-dibenzo[b,d]pyran-9-one A solution of 840 mg. of the 2,2-dimethyl-1,3-propanediol ketal of 4-(1-hydroxy-1-methylethyl)-3-cyclohexen-1-one and 750 mg. of 5-(1,1-dimethylheptyl)resorcinol in 40 ml. of commercial grade dichloromethane was stirred and cooled to −10° C. while 0.82 ml. of stannic chloride was added in one portion. The reaction mixture was then warmed to 0 to 5° C. and stirred for four hours, and then warmed to about 25° C. and stirred for an additional three hours. The reaction mixture next was washed with water and with 1N sodium hydroxide solution, and dried. Removal of the solvent by evaporation under reduced pressure afforded 830 mg. of dl-cis-1-hydroxy-3-(1,1-dimethylheptyl)-6,6-dimethyl-6,6a,7,8,10,10a-hexahydro-9H-dibenzo[b,d]pyran-9-one. The product thus formed was crystallized from 10 ml. of n-hexane. M.P. 159–161° C. GLC demonstrated the product contained 88.8 percent of the title compound.

EXAMPLE 4 dl-cis-1-hydroxy-3-n-pentyl-6,6-dimethyl-6,6a,7,8,10,10a-hexahydro-9H-dibenzo[b,d]pyran-9-one.

A solution of 1.8 g. of 5-n-pentylresorcinol and 2.4 g. of the ethylene ketal of 4-(1-hydroxy-1-methylethyl)-3-cyclohexen-1-one in 50 ml. of dichloromethane was cooled to −10° C. and stirred while 1.8 ml. of stannic chloride was added dropwise to the reaction mixture over fifteen minutes. The temperature of the reaction mixture rose to −4° C. during the addition of the stannic chloride. The reaction mixture was next warmed to 0–5° C. and stirred for six hours. After washing the reaction mixture several times with water, the mixture was dried and the solvent was removed therefrom by evaporation under reduced pressure to provide a residual oil. The oil so formed was crystallized from 5 ml. of methylcyclohexane containing 2 ml. of isopropylalcohol, affording 500 mg. of dl-cis-1-hydroxy-3-n-pentyl-6,6-dimethyl-6,6a,7,8,10,10a-hexahydro-9H-dibenzo[b,d]pyran-9-one. M.P. 152–154° C.

We claim:

1. A ketal of 4-(1-hydroxy-1-methylethyl)-3-cyclohexen-1-one of the general formula

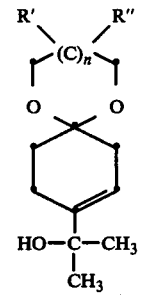

wherein:
n is 1, and
R' and R" independently are hydrogen, methyl or ethyl.

2. The compound of claim 1 wherein R' and R" both are methyl.

3. The compound of claim 1 wherein R' and R" both are hydrogen.

4. The compound of claim 1 wherein R' and R" both are ethyl.

* * * * *